(12) United States Patent
Rikoski

(10) Patent No.: US 10,621,698 B2
(45) Date of Patent: Apr. 14, 2020

(54) SYSTEMS AND METHODS FOR VIRTUAL REALITY MOTION SICKNESS PREVENTION

(71) Applicant: Hadal, Inc., Oakland, CA (US)

(72) Inventor: Richard J. Rikoski, Alameda, CA (US)

(73) Assignee: Hadal, Inc., Oakland, CA (US)

( * ) Notice: Subject to any disclaimer, the term of this patent is extended or adjusted under 35 U.S.C. 154(b) by 0 days.

(21) Appl. No.: 16/009,097

(22) Filed: Jun. 14, 2018

(65) Prior Publication Data

US 2018/0365804 A1    Dec. 20, 2018

Related U.S. Application Data

(60) Provisional application No. 62/519,287, filed on Jun. 14, 2017.

(51) Int. Cl.
| | |
|---|---|
| G06T 3/60 | (2006.01) |
| G09G 5/00 | (2006.01) |
| G06F 3/0346 | (2013.01) |
| G06T 11/60 | (2006.01) |
| G06F 3/147 | (2006.01) |
| G02B 27/01 | (2006.01) |
| A61M 21/00 | (2006.01) |

(52) U.S. Cl.
CPC .............. G06T 3/60 (2013.01); A61M 21/00 (2013.01); G02B 27/017 (2013.01); G06F 3/0346 (2013.01); G06F 3/147 (2013.01); G06T 11/60 (2013.01); G09G 5/003 (2013.01); A61M 2021/005 (2013.01); G09G 2340/0492 (2013.01); G09G 2340/12 (2013.01); G09G 2340/14 (2013.01); G09G 2354/00 (2013.01); G09G 2370/16 (2013.01)

(58) Field of Classification Search
None
See application file for complete search history.

(56) References Cited

U.S. PATENT DOCUMENTS

| | | | |
|---|---|---|---|
| 7,918,781 B1 * | 4/2011 | Smyth | A61M 21/00 600/27 |
| 8,708,884 B1 * | 4/2014 | Smyth | A61M 21/00 600/27 |
| 2002/0099257 A1 | 7/2002 | Parker et al. | |

(Continued)

*Primary Examiner* — Hilina K Demeter
(74) *Attorney, Agent, or Firm* — White & Case LLP

(57) ABSTRACT

Systems and methods are disclosed herein for a sensory compensation device including a position and orientation sensor arranged to generate position and orientation data based on one or more of detected velocity, angular rate, gravity, motion, position and orientation associated with the device. The device also optionally includes an optical sensor arranged to capture real-time images and generate real-time image data of an area adjacent to the device. The device includes a processor arranged to: i) optionally receive the real-time image data, ii) receive the position and orientation data and iii) generate compensated image data based on the real-time image data and the position and orientation data. Furthermore, the device includes a display arranged to display compensated images derived from the compensated image data where a portion of the compensated images includes the captured real-time images, if captured, with adjusted positions and orientations in relation to the captured real-time images.

18 Claims, 8 Drawing Sheets

(56) References Cited

U.S. PATENT DOCUMENTS

| | | | |
|---|---|---|---|
| 2007/0034212 A1 | 2/2007 | Brendley et al. | |
| 2009/0179987 A1* | 7/2009 | Kim | A61M 21/02 348/142 |
| 2011/0282130 A1* | 11/2011 | Krueger | A61M 21/00 600/27 |
| 2013/0038599 A1* | 2/2013 | Krakowski | G06T 11/00 345/419 |
| 2013/0257691 A1* | 10/2013 | Saito | G02B 27/017 345/8 |
| 2014/0055339 A1* | 2/2014 | Stanasolovich | G09G 5/00 345/156 |
| 2014/0152792 A1* | 6/2014 | Krueger | A61M 21/00 348/78 |
| 2014/0176296 A1* | 6/2014 | Morgan | G06F 3/011 340/4.13 |
| 2015/0325027 A1* | 11/2015 | Herman | G06T 13/00 345/633 |
| 2016/0116979 A1* | 4/2016 | Border | G06F 3/013 345/156 |
| 2016/0167672 A1* | 6/2016 | Krueger | H04N 13/366 340/576 |
| 2016/0262608 A1* | 9/2016 | Krueger | A61B 3/0041 |
| 2017/0076496 A1* | 3/2017 | Inomata | G06F 3/012 |
| 2017/0253252 A1* | 9/2017 | Donnelly | B60W 50/0098 |
| 2018/0165878 A1* | 6/2018 | Khan | G06F 3/012 |
| 2018/0181196 A1* | 6/2018 | Lee | H04N 5/23296 |
| 2018/0192058 A1* | 7/2018 | Chen | G06T 11/60 |
| 2018/0286351 A1* | 10/2018 | Fateh | G09G 5/12 |

* cited by examiner

SYSTEMS AND METHODS FOR VIRTUAL REALITY MOTION SICKNESS PREVENTION

REFERENCE TO RELATED APPLICATIONS

This application claims priority to and the benefit of U.S. Provisional Patent Application No. 62/519,287, filed on Jun. 14, 2017, and entitled "Virtual Reality Motion Sickness Prevention." The entire contents of the above-referenced application are incorporated herein by reference.

BACKGROUND

Many people are affected by motion sickness, whether resulting from being at sea (e.g., on a ship, submarine, diving, etc.), from flying, from driving, or even in other circumstances. Motion sickness can be debilitating, resulting in nausea, vomiting and preventing people from carrying out their tasks as planned, whether it be continuing to carry out operations on a submarine, continuing to safely operate a plane, or continuing to enjoy a dive. As described in greater detail in U.S. Pat. No. 5,966,680 (the "'680 patent"), motion sickness results from a mismatch between what motions a person sees happening, and what motions that person internally perceives. Motion sickness can result from a motion felt but not seen, a motion seen but not felt, or different types or amounts of motions being felt and seen. For example, an individual in a ship sees indications of a certain motion or lack thereof in the ship (e.g., the person is in the same reference frame as the objects he sees), but that individual's vestibular system perceives a different motion (e.g., motion of the ship, yawing, pitching or rolling as a whole). Hence, there is a need for enabling a means to compensate for the sensory mismatch leading to motion sickness.

One method for compensating a sensory mismatch, as described in the '680 patent, is a wearable accessory providing visual orientation cues to reflect motion of the user with respect to the environment, in order to train the user's brain to correct the sensory mismatch, i.e. to correct what the user perceives. In an alternative embodiment, the '680 patent displays no visual cues, but records an image and averages it with other images so as to produce what is perceived by the user to be a slowly changing display of the visual environment, projected onto glasses, effectively minimizing the magnitude of any observed movement. Yet, such a device and its visual cues require additional user training and user experience to enable users to properly account for cues to alleviate the effects caused by sensory mismatches.

Accordingly, there remains a need to provide persons subject to the adverse effects of sensory mismatch with systems, methods, and devices that more naturally and readily enable a user to overcome perception mismatches leading to such adverse effects.

SUMMARY

Systems and methods are disclosed herein for providing virtual reality and/or augmented reality mechanisms to alleviate or mitigate effects caused by a person's sensory mismatch of their perceived surroundings. According to one aspect, a sensory compensation device includes a position and orientation sensor arranged to generate orientation and acceleration data based on one or more of detected velocity, angular rate, gravity, motion, position, acceleration, and orientation associated with the device. In some implementations, the device includes an optical sensor arranged to capture real-time images and generate real-time image data of an area adjacent to the device. The device further includes a processor arranged to: i) receive the real-time image data, ii) receive the orientation and acceleration data and iii) generate compensated image data based on the real-time image data and the orientation and acceleration data. The device includes a display arranged to display compensated images derived from the compensated image data such that a portion of the compensated images includes the captured real-time images with adjusted orientations and accelerations in relation to the captured real-time images.

The orientation and acceleration data may include at least one of roll, pitch, and yaw data in relation to an inertial reference point. The inertial reference point may include a reference horizon. The orientation and acceleration data may include a differential position between the inertial reference point and a detected orientation and acceleration of the device. The portion of compensated images may be adjusted proportional to the differential position between the inertial reference point and the detected position and orientation of the device. The portion of compensated images may be adjusted in a reciprocal direction or orientation as the direction or orientation of the detected differential position. The portion of compensated images may be rolled clockwise by one or more degrees proportional to a detected roll of the device by the one or more degrees in a counterclockwise direction.

The device may be head-mounted, hand-held, or detachably connectable to an optical system. The optical system or instrument may include eyeglasses. The display may include LCD, LED, liquid crystal on silicon (LCoS), and/or OLED elements. The display may include a computer monitor, television, mobile device display, computer tablet display, projection from a projector onto a portion of a wall or bulkhead, and/or any other visual display apparatus.

The area adjacent to the device may include at least one of an area forward, behind, and at a side of the device. The optical sensor may include at least one video camera. The compensated image data may include data that enables the display of at least one of an overlay, background, and shadow image with respect to the captured real-time images. At least one of the overlay, background, or shadow image may include at least one of a reference horizon and sky. The sky may be a night sky including one or more stars.

In another aspect, a sensory compensation device includes an orientation and acceleration sensor arranged to generate orientation and acceleration data based on one or more of detected velocity, angular rate, gravity, motion, position, acceleration, and orientation associated with the device. The device includes an optical element through which a user views an area adjacent to the device. The device also includes a processor arranged to: i) receive the orientation and acceleration data and ii) generate orientation and acceleration image data. The device further includes a display arranged to display orientation and acceleration images derived from the orientation and acceleration image data to the user via the optical element such that the orientation and acceleration images include one or more features having adjusted orientations and accelerations in relation to the view of the area adjacent to the device.

The position and orientation image data may include data that enables the display of at least one of an overlay image on the view of the area adjacent to the device via the optical element. The overlay may include at least one of a reference horizon and sky.

In another aspect, a computing device includes an orientation and acceleration sensor arranged to generate orientation and acceleration data based on one or more of detected velocity, angular rate, gravity, motion, acceleration and orientation associated with the device. The device also includes a processor arranged to: i) receive the orientation and acceleration data and ii) generate compensated image data based on the orientation and acceleration data. The device further includes a display arranged to display compensated images derived from the compensated image data, where a portion of the compensated images include one or more features having adjusted orientations and accelerations in relation to a user's view of the area adjacent to the device. The device may be a computer desktop, laptop, mobile device, computer where the display is projected via a projector, or a portable computer tablet.

In a further aspect, a hand-held mobile computing device includes an orientation and acceleration sensor arranged to generate position and orientation data based on one or more of detected velocity, angular rate, gravity, motion, position, acceleration, and orientation associated with the device. The device includes an optical sensor arranged to capture real-time images and generate real-time image data of an area adjacent to the device. The device also includes a processor arranged to: i) receive the real-time image data, ii) receive the orientation and acceleration data and iii) generate compensated image data based on the real-time image data and the orientation and acceleration data. The device further includes a display arranged to display compensated images derived from the compensated image data such that a portion of the compensated images includes the captured real-time images with adjusted orientations and accelerations in relation to the captured real-time images.

Other objects, features, and advantages of the present invention will become apparent upon examining the following detailed description, taken in conjunction with the attached drawings.

BRIEF DESCRIPTION OF THE DRAWINGS

The systems and methods described herein are set forth in the appended claims. However, for purpose of explanation, several illustrative aspects are set forth in the following figures.

DETAILED DESCRIPTION

To provide an overall understanding of the invention, certain illustrative aspects will now be described. However, it will be understood by one or ordinary skill in the art that the systems and methods described herein can be adapted and modified for other suitable applications and that such other additions and modifications will not depart from the scope hereof.

Individuals can be affected by motion sickness in moving vehicles such as cars, trains, boats, ships, and airplanes. The effects of motion sickness can be severe and disabling. Motion sickness is often caused by a sensory mismatch between a person's visual perception of their surroundings and perceived motion via the person's inner ear (e.g., vestibular system) and brain. In such circumstances, the person's brain cannot reconcile one's sensed motion with what the person's eyes are seeing. Vertigo is one type of sensor mismatch where the body perceives motion when there is actually no motion, and attempts to counteract such perceived motion by changing the body's posture.

Figure 1:
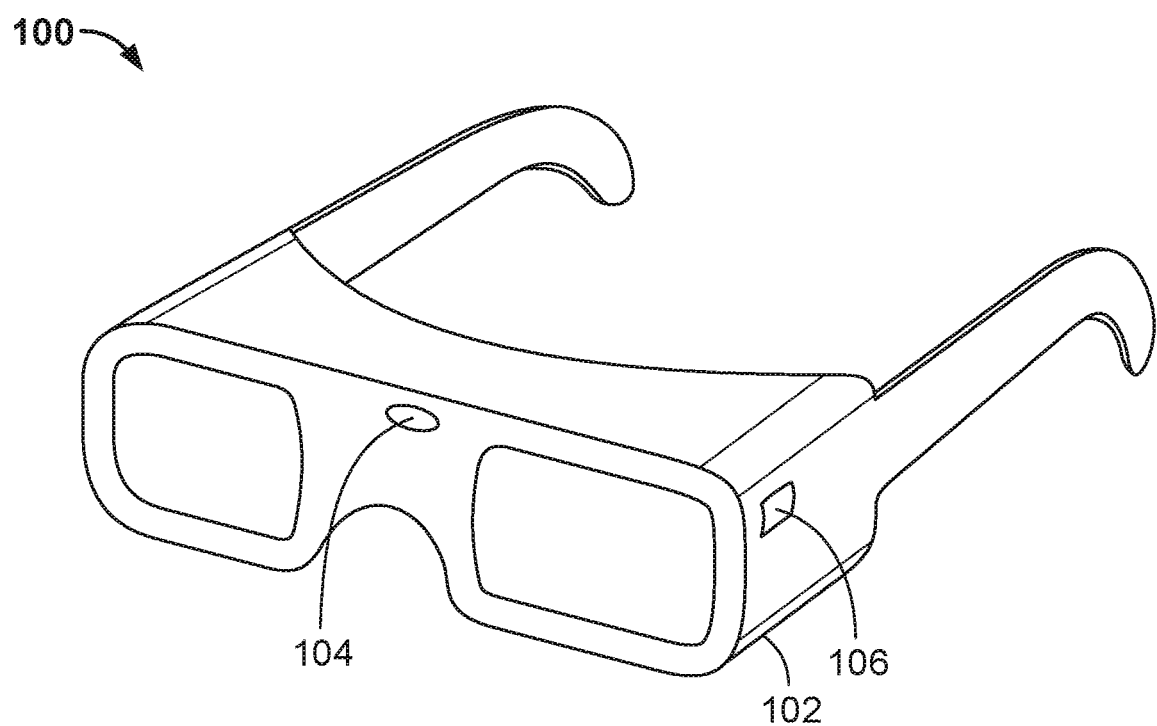
FIG. 1 depicts an optical device arranged to display an image to a user or augment a user's existing visual perception of their surroundings.

FIG. 1 depicts an optical device 100 arranged to display an image to a user or augment a user's existing visual perception of their surroundings. The device 100 may include a housing 102 arranged to cover the eyes of a user while providing a one or more display elements that display images and other information to the user. The device may include an optical sensor 104 such as a video camera arranged to capture real-time video images in an area adjacent to the device 100 such as in front of, behind of, or next to the device 100. The device 100 may include an orientation and acceleration sensor 106, e.g., an accelerometer to detect velocity, angular rate, gravity, motion, position, acceleration, and/or orientation associated with device 100. The device 100 may include a computer system such as described with respect to FIG. 2. In some implementations, the device 100 may include a pair of eyeglasses. In such a configuration, the device 100 may not implement optical sensor 104 because the user will be able to view the area in front of the device 100 through the optical elements, eyeglasses, of the device 100. The device 100 may include a display projected onto a surface of the eyeglasses or directly to an eye or eyes of the user to present orientation and acceleration images to a user. In one aspect, device 100 may include a computer, a laptop, or a tablet.

The orientation and acceleration sensor 106 may include at least one accelerometer. The accelerometer may detect Earth's gravity based on detecting an acceleration due to the Earth's gravity straight downwards of about 9.81 m/s$^2$ at the Earth's surface. An accelerometer may be used to determine the Earth's reference horizon because gravity always acts perpendicular to the Earth's surface. The reference horizon may be referred to as the line at which the Earth's surface and the sky appear to meet. In some implementations, the accelerometer includes a three-access accelerometer. In some implementations, a sensor including an accelerometer or other positional sensing element (or a processor receiving sensor data) may establish an inertial reference point from which subsequent displays to a user are adjusted based on sensed changes in position, acceleration, and/or orientation with respect to the inertial reference point. One component of the reference point may include a plane corresponding to the Earth's horizon.

Figure 2:
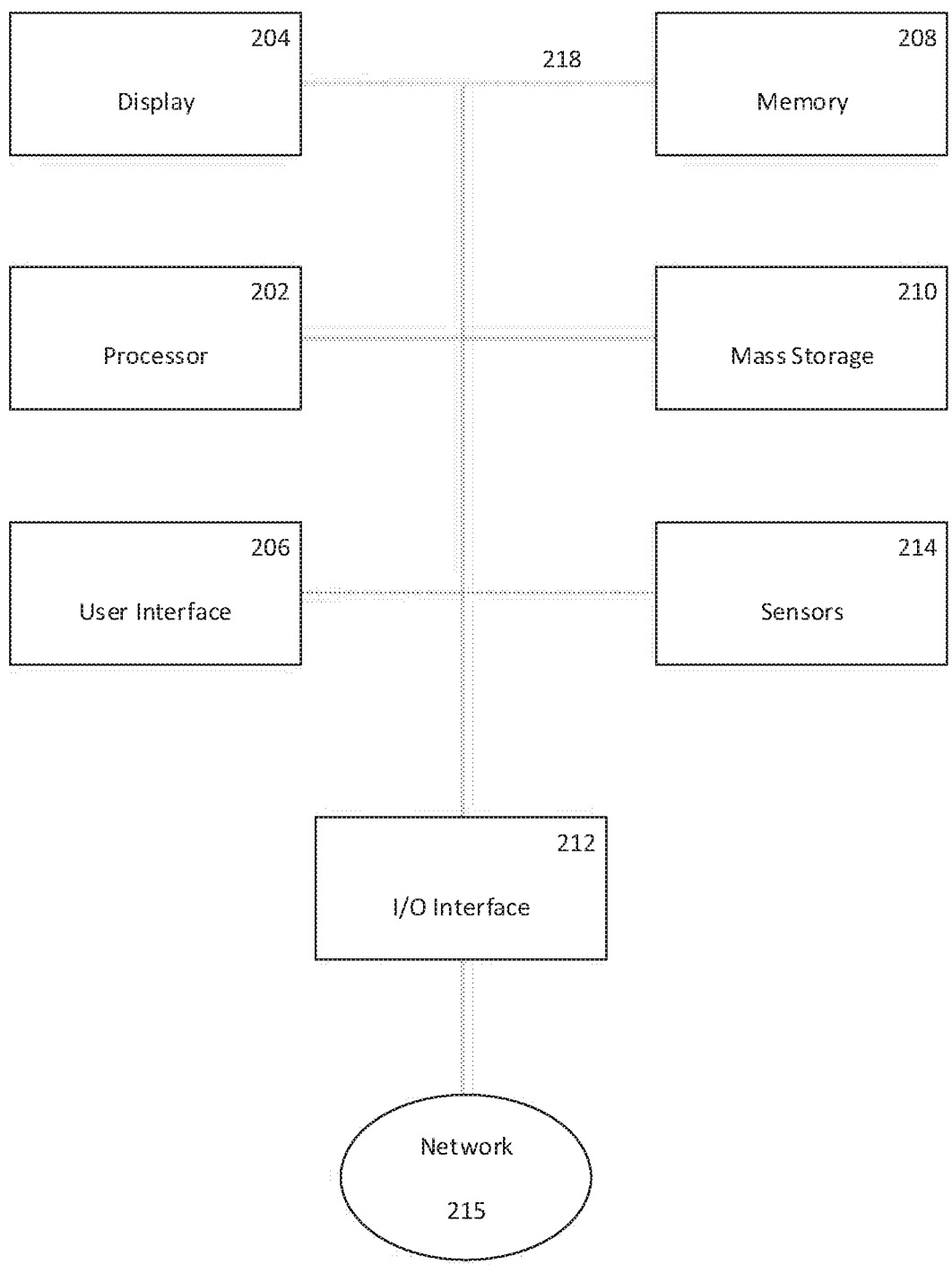
FIG. 2 is block diagram of an exemplary computer system for implementing at least a portion of the systems and methods described herein.

FIG. 2 is block diagram of an exemplary computer system 200 for implementing at least a portion of the systems and methods described herein, including implementation computer processing in device 100. The exemplary system 200 includes a processor 202, a memory 208, and an interconnect bus 218. The processor 202 may include a single microprocessor or a plurality of microprocessors for configuring computer system 200 as a multi-processor system. The memory 208 illustratively includes a main memory and a read-only memory. The system 200 also includes the mass storage device 210 having, for example, various disk drives, tape drives, etc. The main memory 208 also includes dynamic random access memory (DRAM) and high-speed cache memory. In operation and use, the main memory 208 stores at least portions of instructions for execution by the processor 202 when processing data (e.g., model of the terrain) stored in main memory 208.

In some aspects, the system 200 may also include one or more input/output interfaces for communications, shown by way of example, as interface 212 for data communications via the network 216. The data interface 212 may be a modem, an Ethernet card or any other suitable data communications device. The data interface 212 may provide a relatively high-speed link to a network 216, such as an intranet, internet, or the Internet, either directly or through another external interface. The communication link to the network 216 may be, for example, any suitable link such as an optical, wired, or wireless (e.g., via satellite or 802.11 Wi-Fi or cellular network) link. In some aspects, communications may occur over an acoustic modem. For instance, for AUVs, communications may occur over such a modem. Alternatively, the system 200 may include a host computer system capable of web-based communications via the network 216. In some aspects, the system 200 also includes suitable input/output ports or may use the Interconnect Bus 218 for interconnection with a local display 204 and user interface 206 (e.g., keyboard, mouse, touchscreen) or the like serving as a local user interface for programming and/or data entry, retrieval, or manipulation purposes. Alternatively, server operations personnel may interact with the system 200 for controlling and/or programming the system from remote terminal devices (not shown in the Figure) via the network 216.

In some aspects, a system requires a processor, such as in device 100, coupled to one or more sensors (e.g., optical sensor 104 and orientation and acceleration sensor 106). Data corresponding to sensed or detected information by sensor 104 and/or sensor 106 may be stored in the memory 208 or mass storage 210, and may be retrieved and/or received by the processor 202. Processor 202 may execute instructions stored in these memory devices to perform any of the methods described in this application, e.g., sensory compensation and/or generation of modified, adjusted and/or compensated displays of images to a user.

The system may include a display 204 for displaying information, a memory 208 (e.g., ROM, RAM, flash, etc.) for storing at least a portion of the aforementioned data, and a mass storage device 210 (e.g., solid-state drive) for storing at least a portion of the aforementioned data. Any set of the aforementioned components may be coupled to a network 216 via an input/output (I/O) interface 212. Each of the aforementioned components may communicate via interconnect bus 218.

In some aspects, the system requires a processor coupled to one or more sensors. The sensor 104 may include one or more image capture components and/or video cameras. The sensor 106 may include one or more inertial detection elements such as, for example, one or more accelerometers or one or more gyroscopes.

Data corresponding to sensed video images and/or sensed orientation and acceleration, and/or changes in position, orientation, and acceleration, and a process for providing sensory compensation to a user or users may be performed by a processor 202. The system may include a display 204 for displaying information, a memory 208 (e.g., ROM, RAM, flash, etc.) for storing at least a portion of the aforementioned data, and a mass storage device 210 (e.g., solid-state drive) for storing at least a portion of the aforementioned data. Any set of the aforementioned components may be coupled to a network 216 via an input/output (I/O) interface 212. Each of the aforementioned components may communicate via interconnect bus 218. Orientation and acceleration data may include data based on detected velocity, angular rate, gravity, motion, position, acceleration, and orientation associated with the device.

In operation, a processor 202 receives data from the sensor(s) 104 and/or 106, calculates a change in orientation and/or acceleration of the device 100 and user, and then modifies and/or adjusts aspects or portions of a images presented to the user as described herein to reduce possible adverse effects of sensory mismatches between the user's visual perception and inner ear. Optionally, the processor 202 may receive additional information from a vessel in which, for example, the device 100 is located. The additional information may include, for example, navigational information, ship's status information, and/or altitude information, and a processor 202 may include a portion of such information and/or information as described in the '680 patent. The output from the system processor 202 may directed to the display 204 and/or transmitted to another display external to device 100, e.g., a ship's control room display.

The components contained in the system 200 are those typically found in general purpose computer systems used as servers, workstations, personal computers, network terminals, portable devices, mobile devices and the like. In fact, these components are intended to represent a broad category of such computer components that are well known in the art.

It will be apparent to those of ordinary skill in the art that methods involved in the systems and methods of the invention may be embodied in a computer program product that includes a non-transitory computer usable and/or readable medium. For example, such a computer usable medium may consist of a read only memory device, such as a CD ROM disk, conventional ROM devices, or a random access memory, a hard drive device or a computer diskette, a flash memory, a DVD, or any like digital memory medium, having a computer readable program code stored thereon.

Optionally, the system 100 and/or 200 may include an inertial navigation system, a Doppler sensor, an altimeter, a gimbling system to fixate the sensor on a populated portion of a holographic map, a global positioning system (GPS), a long baseline (LBL) navigation system, an ultrashort baseline (USBL) navigation, or any other suitable navigation system.

Figure 3A:
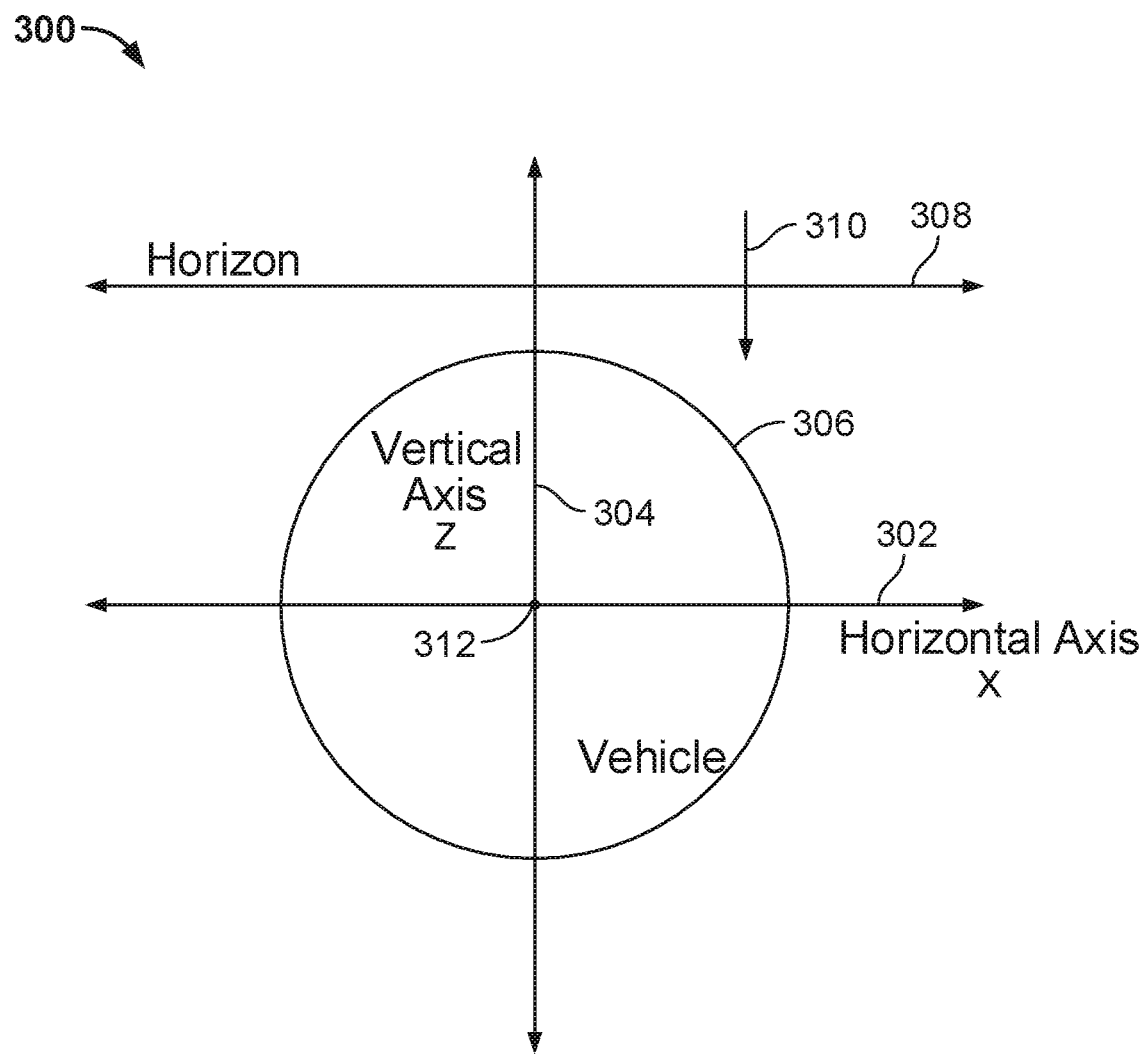
FIG. 3A is a conceptual diagram showing vertical and horizontal axes associated with a vehicle in relation to a horizon.

FIG. 3A is a two-dimensional cross-sectional diagram 300 showing vertical axis 304 (the "Z" axis) and a horizontal axis 302 (the "X" axis) associated with a vehicle 306 in relation to a reference horizon 308. Although not shown, there is a "Y" axis extending through the center of vehicle 306 (i.e., a submarine's hull) from bow to stern intersecting the center point 312. For a vessel riding on the surface of an ocean, the horizontal axis 302 should generally be parallel to the Earth's horizon or reference horizon 308. Also, the reference horizon 308 should be perpendicular to the Earth's gravity 310, which has an acceleration relatively straight downward at the ocean surface.

Figure 3B:
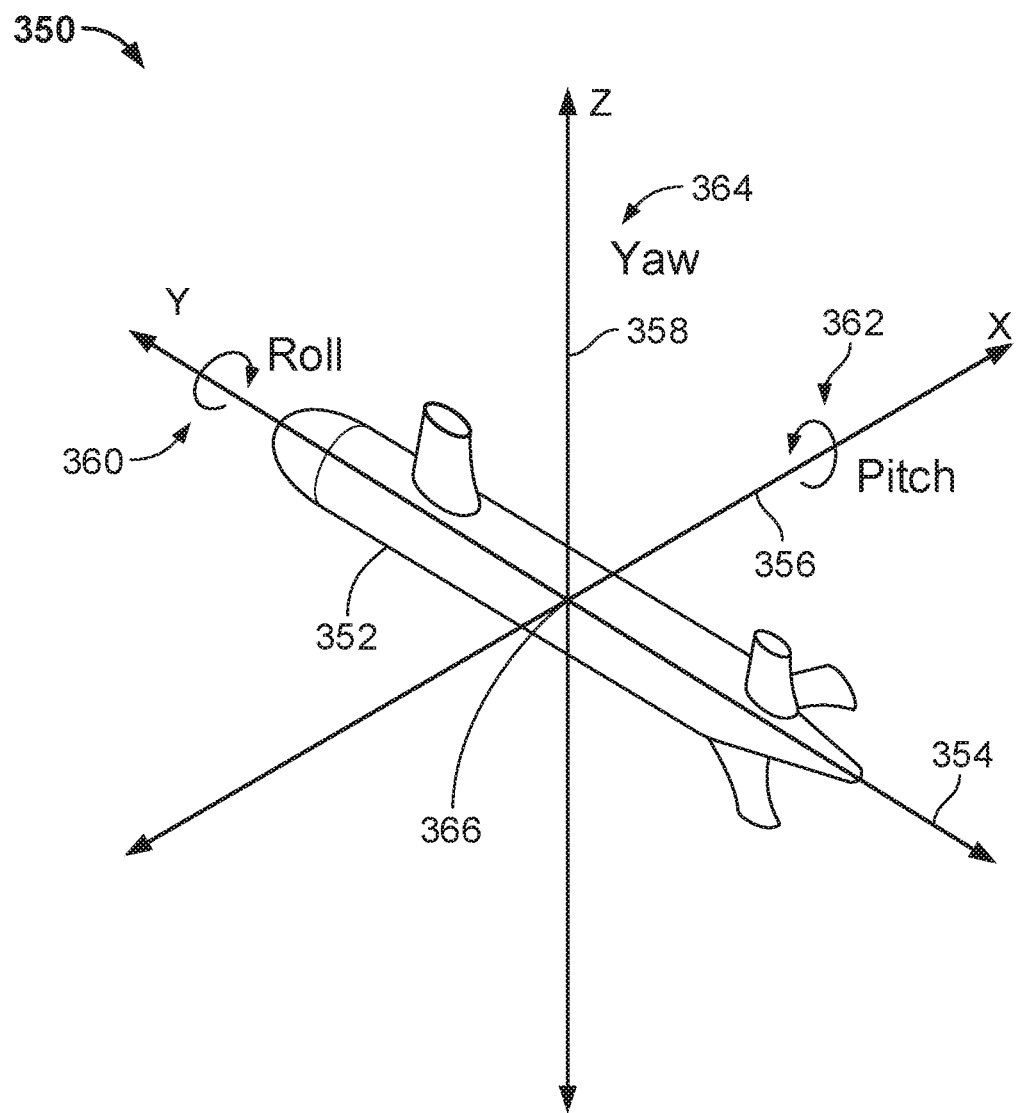
FIG. 3B is a conceptual diagram illustrating pitch, roll, and yaw associated with a submarine.

FIG. 3B is a three-dimensional conceptual diagram 350 illustrating pitch, roll, and yaw associated with a submarine 352. Assuming that the submarine 352 is moving in the direction of the "Y" axis 354, roll 360 represents the rotation or rotational orientation of the submarine along its bow-to-stern axis 354. Pitch 362 represents the submarine's rotation or rotational orientation along its "X" axis 356 that extends perpendicularly from a center point 366 of the submarine 352, but also in a substantially parallel direction as the horizon 308. Yaw 364 represents the submarines rotation along its "Z" axis 358 which extends in a substantially perpendicular direction to the reference horizon 308. A plane defined by the "X" axis 356 and "Y" axis 354 may also generally lie in parallel to the reference horizon 308 at least within the vicinity of the submarine 352. In some configurations, the orientation and acceleration sensor 106 senses, detects, and/or measures the roll 360, pitch 362, and/or yaw 364 associated with device 100 while being located within the submarine 352 as the submarine 352 moves through the water and experiences changes in orientation and acceleration due to its surrounding environment.

The device 100 may include an orientation and acceleration sensor arranged to generate orientation and acceleration data based on one or more of detected velocity, angular rate, gravity, motion, position, acceleration, and orientation associated with the submarine 352 and, therefore, the device 100 because the device 100 is located in the submarine 352. However, the degree of changes in pitch 362 may vary depending on the location of the device 100 within the submarine 352. The sensor 106 may detect changes in roll 360, pitch 362, and/or yaw 364 in relation to an inertial reference point such as a reference in relation to a determined reference horizon 308, which may be included in the orientation and acceleration data. For example, the determined inertial reference point may correspond to the center point 366 of submarine 352. The inertial reference point may be stationary or relative. For example, submarines may use a stationary inertial reference point to enable underwater navigation over long or short distances. The submarine may periodically reset its inertial reference point by going to the surface and, for example, using GPS information to calibrate or adjust its location information derived from inertial sensors. An inertial reference may be relative with respect to, for example, the Earth's horizon or a reference horizon 308 which may be determined, for example, by detecting the Earth's gravitational acceleration. An inertial reference point may be established by device 100 when, for example, the device experiences less than a threshold of acceleration. For example, when submarine 352 is stationary in calm waters, the sensor 106 may only substantially detect the Earth's gravitational acceleration.

The device 100 may use an optical sensor to capture real-time images and generate real-time image data of an area adjacent to the device. The device 100 may include a processor arranged to: i) receive the real-time image data, ii) receive the orientation and acceleration data and iii) generate compensated image data based on the real-time image data and the orientation and acceleration data. The device 100 may include a display, e.g., display 205, that displays compensated images derived from the compensated image data such that a portion of the compensated images includes the captured real-time images with adjusted orientations and accelerations in relation to the captured real-time images.

For a person on the submarine 352, the submariner's eyes are locked on what they see within the local reference frame of the submarine: a visual reference frame, e.g., a room, table, instruments, etc. When the submarine moves, i.e. yaws, pitches or rolls, what the person sees (their visual reference frame of the submarine) does not match what they feel: an inertial reference frame. In one implementation, a virtual reality system, e.g., device 100, displays to the user images adjusted to match the user's inertial reference frame.

Figure 4B:
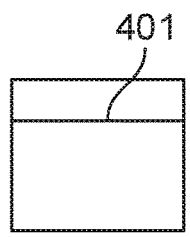
FIG. 4B illustrates a horizon.
Figure 4A:
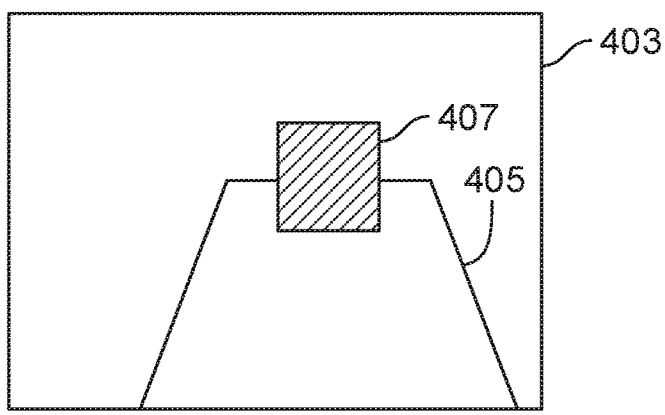
FIG. 4A shows a display of an image provided by an optical device.

FIG. 4A shows a reference horizon 401. FIG. 4B shows a view 403 seen by a user, including an object 407 positioned on a surface 405. Because the submarine is level, the reference horizon 401 is level, and the view 403 is also level—there is no sensory mismatch.

Figure 5B:
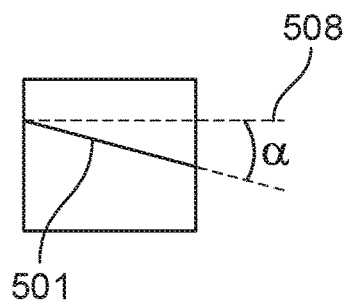
FIG. 5B illustrates a change in roll in relation to a horizon.
Figure 5A:
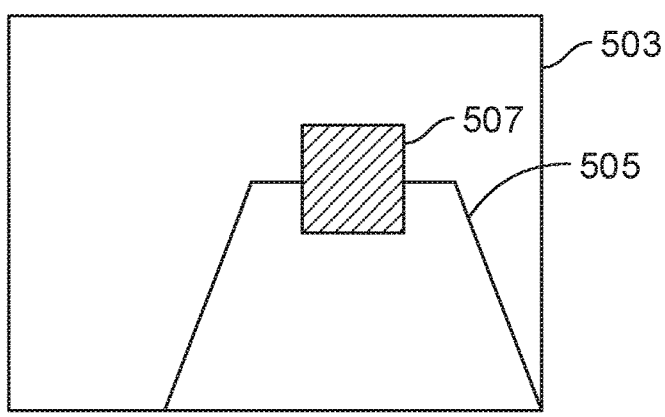
FIG. 5A shows a display of an uncompensated image or direct visual perception when a roll by a degree alpha occurs

FIG. 5A shows a reference horizon 501 (i.e., the Earth's horizon) which is inclined relative to a horizontal axis 508, i.e., "X" axis 356 of FIG. 3B, by an angle alpha, reflecting that the submarine has now rolled counterclockwise by this angle alpha. As a result, because the user is positioned on the submarine 352, FIG. 5B shows the view 503 seen by the user still includes both the surface 505 and the object 507 positioned on that surface that appears level, even though the surface or deck is actually tilted (rolled) by alpha degrees in the counterclockwise direction. The mismatch between the view 503 seen by the user, and the actual orientation of the submarine 352, reflected by the angle alpha of the reference horizon 501, is what leads to motion sickness. Additionally, the rate of change of the angle and/or acceleration of change can contribute to motion sickness The present invention is not limited to roll by an angle alpha—any type of movement including any combinations of yaw, pitch, roll, along with any translational motion may be adjusted for, as further described.

Figure 6B:
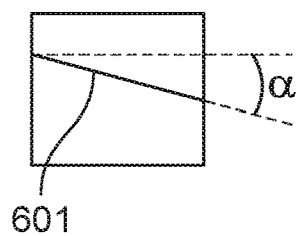
FIG. 6B illustrates the change in roll in relation to the horizon.
Figure 6A:
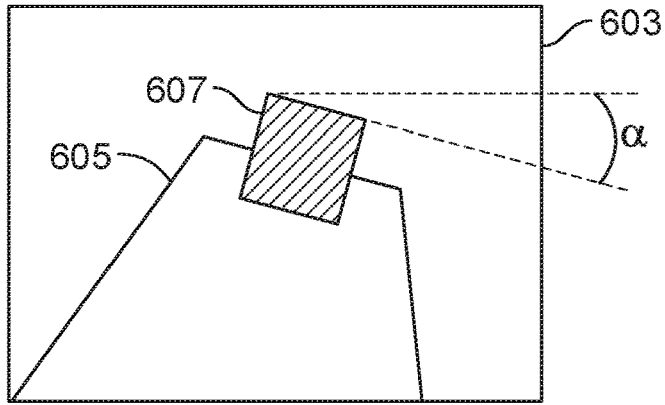
FIG. 6A shows a display of a compensated image when a counterclockwise roll of alpha degrees is detected.

FIGS. 6A and 6B illustrate how a compensated image may be used to alleviate the adverse effects of sensory mismatches according to the present invention. In this implementation, FIG. 6B shows the reference horizon 601 is still inclined by an angle alpha, indicating again that the submarine rolled counterclockwise by this angle alpha. The system and/or device 100 records video of what optical sensor 104 captures, e.g., what the user would see in FIG. 5 when the submarine rolls counterclockwise. The system further detects through one or more sensors 106 (e.g., accelerometers) the counterclockwise roll of the ship by an angle alpha. The system further processes the recorded video before displaying the processed video in real-time or near-real time to the user, to match the detected movement, as shown in the view 603 that the user is now seeing. The processed video (e.g., the recorded video rotated by the same angle alpha, but in the clockwise direction), also referred to as compensated images, is generated for display in real-time or near-real time to the user, such that the user sees what is shown in FIG. 6A. Because what the user sees (e.g., a roll by an angle alpha) reflects what the user feels (e.g., a roll of the submarine by that angle alpha), motion sickness can be avoided. In other words, the tilt or roll by alpha degrees on objects 605 and 607 gives the visual sensation to the user of tilt or roll in the counterclockwise direction by alpha degrees, which corresponds to the user's sensation of a counterclockwise roll. One technical advantage of this implementation includes, for example, a capability for a sailor to more efficiently review documents on a ship in turbulent waters. The virtual reality system, worn by the sailor, detects the ship's movements in the turbulent waters, and adjusts the display of the documents to match the submarine movements. Because what the sailor sees (the processed display of the documents), matches what is perceived by the sailor's vestibular system (movement of the ship in turbulent waters), including changes in angles at certain rates and/or accelerations, motion sickness and its side effects can be avoided.

Processing of the recorded video may include parsing certain portions of the recorded video and rotating, scaling, or otherwise adjusting one or more portions of the recorded video. Similarly, processing of the recorded video may also include parsing certain sequences of the recorded video, and rotating, scaling, or otherwise adjusting one or more time segments of the recorded video. In some embodiments, the processed video may be displayed to the user through a virtual reality device, such as the Microsoft Oculus VR headset, an augmented reality device or any other virtual reality headset (e.g., device 100). In some embodiments, the processed video may be generated for display through goggles compatible with any handheld mobile device, such as a phone or tablet. In some embodiments, the processed video may be generated for display as a 3D environment. In some embodiments, the processed video may be generated for display in a spherical display, with different tiles showing different views, the system automatically adjusting the position of the titles as a function of the detected user's movement, such that the user is shown the one or more tiles best corresponding to the movement that user is experiencing. In some embodiments the tiles may show the same view so that as one tile rotates out of the field of view the user can refocus on a tile moving into the field of view and continue their activity. In some embodiments the tiles may show a computer desktop with applications. In some embodiments the tiles may show a Unix terminal, an Emacs window, or a Microsoft Word document. In some embodiments the tiles may show an integrated development environment such as an Eclipse that allows the user to program in computer languages such as C++ or Java.

Figure 7:
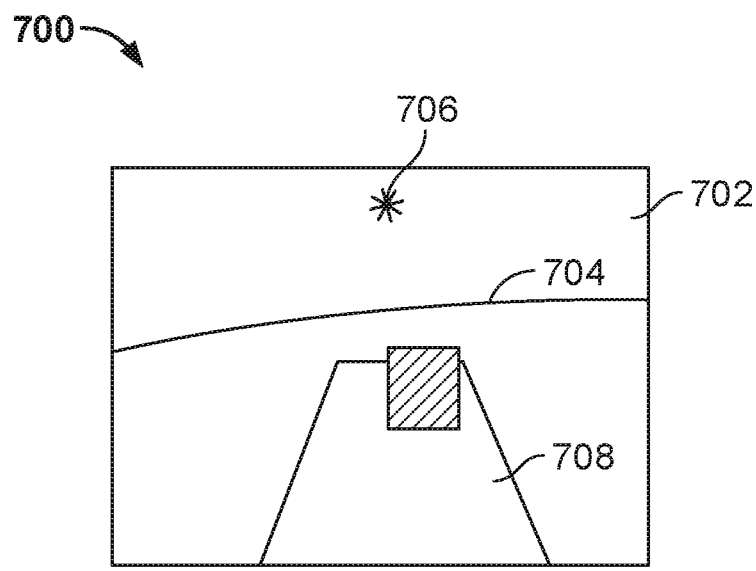
FIG. 7 is another display of an image including a horizon and night sky with at least one star or an overlay of a horizon and night sky with at least one star over a user's perceived field of view.

FIG. 7 is another display of an image 700 including a reference horizon 704 and night sky 702 with at least one star 706 or an overlay on a user's direct view through an optical instrument (e.g., eyeglasses) including a reference horizon 704 and night sky 702 with at least one star 706. In one configuration, device 100, operating as a VR headset, displays image 700. In a submarine or an enclosed space in a ship or plane, a user is unable to perceive the Earth's horizon. In FIG. 7, the device 100 displays a view of the area in front of the device 100 based on video images captured by optical sensor 104. The originally captured video images and data from sensor 104 have been modified to include a reference horizon 704 and/or sky 702. The horizon 704 may be displayed as an overlay, shadow, or background in relation to the originally captured video images from sensor 104. The reference horizon 704 and/or sky 702 enable a viewer to visually perceive changes in the orientation and acceleration of the submarine (or other vessel) that correlate with the viewer sensation of changes by their inner ear to alleviate motion sickness.

Figure 8:
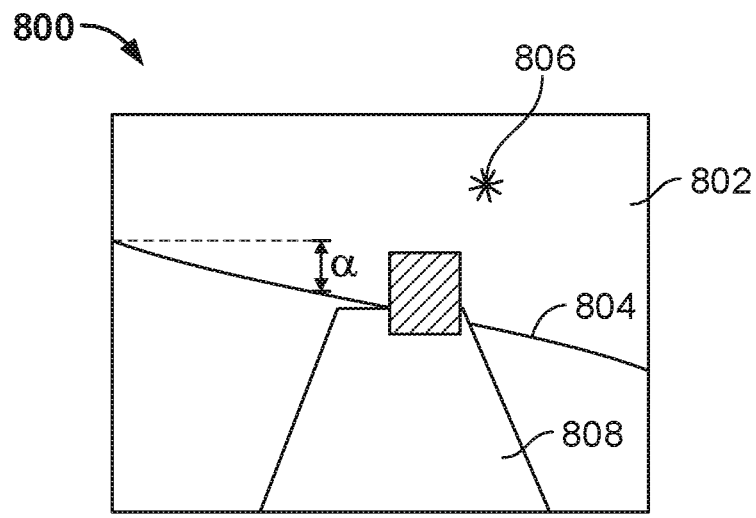
FIG. 8 is a display of an image including a horizon and night sky with at least one star when a detected roll of alpha degrees is detected or an overly of a horizon and night sky with at least one star over a user's perceived field of view.

FIG. 8 is a display of an image 800 including a reference horizon 804 and night sky 802 with at least one star 806 when a roll of alpha degrees is detected. The reference horizon 804 and/or sky 802 enable a viewer to visually perceive the roll of the submarine (or other vessel) by alpha degrees by showing a tilt or roll of the horizon 804 by alpha degrees. This enable viewer to correlate their visual perception with their motion sensations by their inner ear to alleviate motion sickness. Again, the originally captured video images and data from sensor 104 have been modified to include a reference horizon 804 and/or sky 802 that are tilted by alpha degrees. The horizon 804 may be displayed as an overlay, shadow, or background in relation to the originally captured video images from sensor 104.

FIG. 8 also illustrates overlay on a user's direct view through an optical instrument (e.g., eyeglasses) including a reference horizon 804 and night sky 802 with at least one star 806. In this implementation, the device 100 is configured to allow the viewer to directly view an area adjacent to them (i.e., in front of them), but the device 100 provided an overlay with respect to at least one eye of the view that displays the horizon 804, sky 802, and/or star 806. In a further implementation, the device 100 is configured as an attachably disconnectable unit capable of physical attachment to eyeglasses whereby an overlay of the horizon 804, sky, and/or start 806 are displayed to at least one eye of a viewer using the eyeglasses. Instead of modifying the position, acceleration, and orientation of objects as described with respect to FIGS. 6A and 6B, features are added to the captured image or overlaid onto a direct view via an optical instrument to enable a viewer to perceive the orientation and acceleration of the reference horizon which should always correlate with the viewer's perceived vestibular orientation and acceleration.

The change in orientation and acceleration displayed detected may be displayed proportionally by device 100. For example, a detected change in pitch of beta degrees may be displayed as a change in pitch by beta degrees. Optionally, the display change may be a fraction or portion of the detected change in pitch, roll, and/or yaw. Although FIGS. 6B and 8 are examples of how the device 100 processes rolls, device 100 applies similar techniques with respect to detected changes in pitch and yaw. In certain implementations, device 100 concurrently detects and processes changes in roll, pitch, and yaw, and generates compensated images based on the combination of changes associated with roll, pitch, and yaw.

Figure 9:
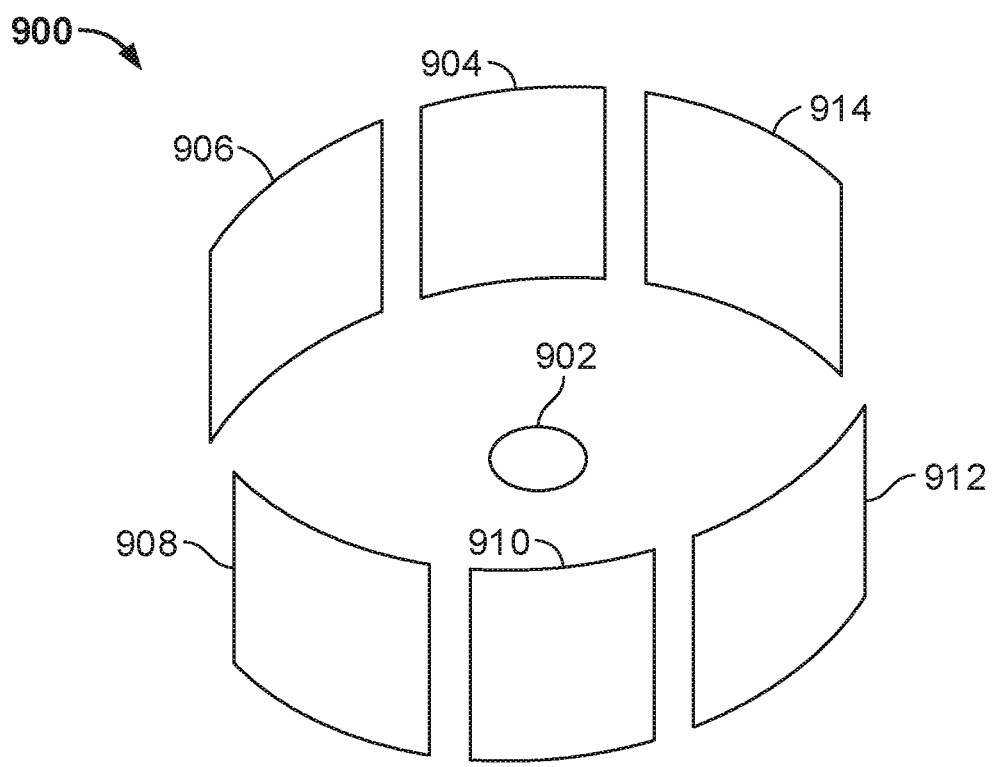
FIG. 9 depicts a virtual or augmented reality space surrounding a user including multiple virtual displays in various positions around the user.

FIG. 9 depicts a virtual or augmented reality space 900 spherically surrounding a viewer 902 of device 100 including multiple virtual displays or tiles 904, 906, 908, 910, 912, and 914 in various positions around the viewer. In some implementations, the processed video or compensated images may be generated for display in a spherical display, with different tiles showing different views, the system may automatically adjust the position of one or more of the titles as a function of the device's or viewer's movement, such that the viewer is shown the one or more tiles best corresponding to the movement that viewer is experiencing. The position, acceleration, and orientation of each tile may be modified in response to detected changes in roll, pitch, and yaw. For example, if device 100 detects a pitch downward of beta degrees, the tile 904 may be shifted upward by beta degree correspondingly to give the visual impression of movement upward to user 902 which will correspond to the user's vestibular sensation of a downward pitch. In some implementations, the image a tile 904, 906, 908, 910, 912, and/or 914 may be modified, adjusted, or compensated in a manner described with respect to FIG. 6B or 8.

Figure 10:
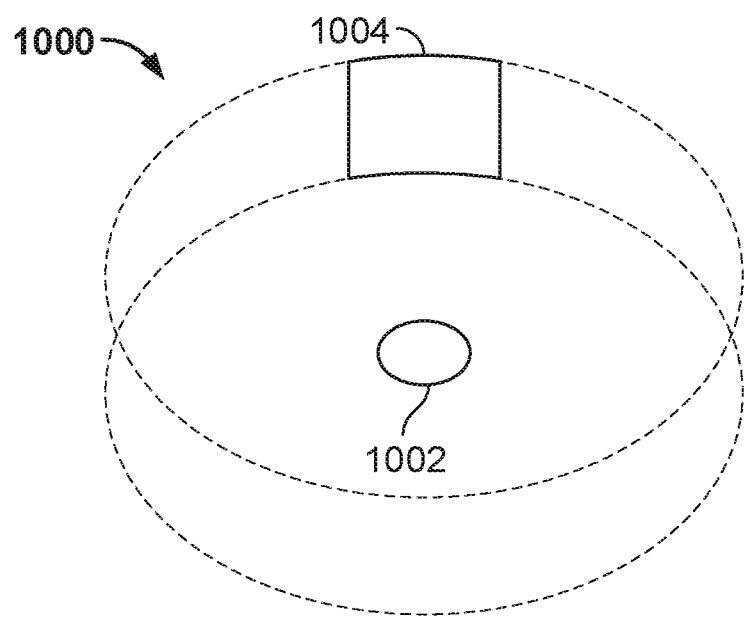
FIG. 10 depicts a virtual or augmented reality space surrounding a user including a display capable of being extended continuously around a user.

FIG. 10 depicts a virtual or augmented reality space 1000 surrounding a viewer 1002 including a display 1004 capable of being virtually extended continuously around the viewer 1002. Instead of presenting multiple tiles, device 100 may virtually stitch together multiple tiles such as tiles 904-914 to provide a more seemly transition among the different tiles. Portions of the display 1004 may shift in position, acceleration, and orientation in a similar manner as the tiles in FIG. 9. The techniques described with respect to FIGS. 6A-10 may be applied using a hand-held mobile device using an augmented reality application. For instance, a mobile device with a camera may be held by a viewer that views the touch screen. The camera may capture real-time video and display the captured video on the display, while the processor, running a sensory compensation application, overlays a reference horizon and/or sky onto the displayed image.

Figure 11:
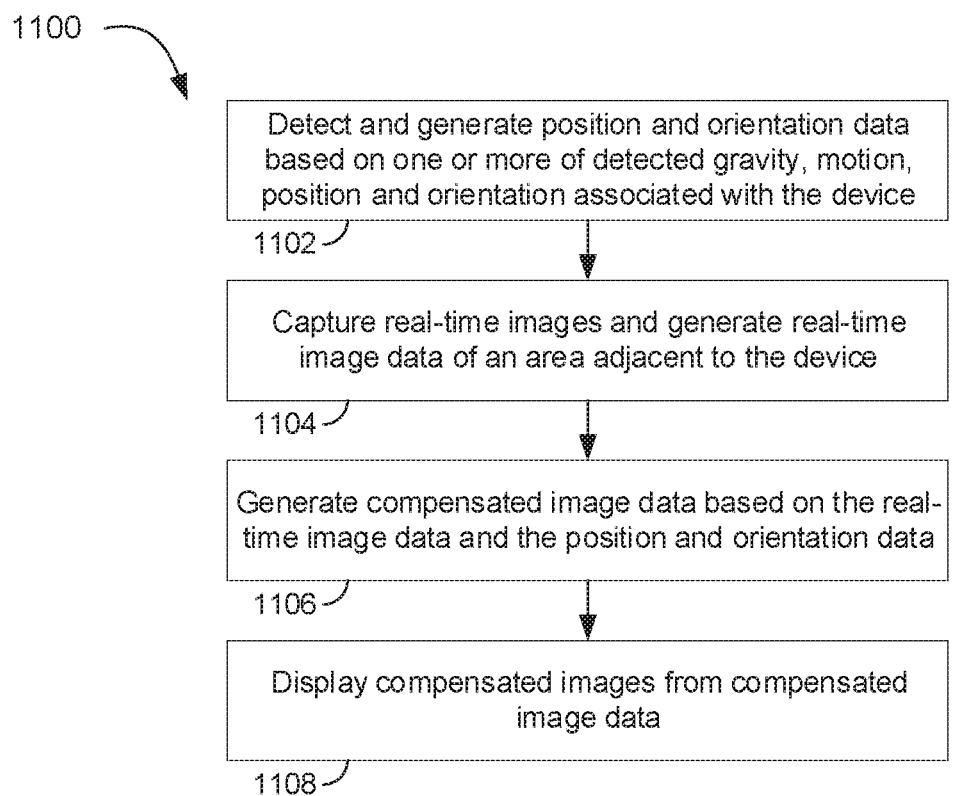
FIG. 11 is an exemplary process according to a method of alleviating the adverse effects of a sensory mismatch.

FIG. 11 is an exemplary process 1100 for alleviating the adverse effects of a sensory mismatch. First, generate orientation and acceleration data based on one or more of detected velocity, angular rate, gravity, motion, position, acceleration, and orientation associated with the device 100 using a sensor 106 (Step 1102). Capture real-time images using an optical sensor 104 and generate real-time image data of an area adjacent to the device (Step 1104). Using a processor, receive the real-time image data, receive the orientation and acceleration data and generate compensated image data based on the real-time image data and the orientation and acceleration data (Step 1106). Then, display compensated images derived from the compensated image data such that a portion of the compensated images includes the captured real-time images with adjusted orientations and accelerations in relation to the captured real-time images (Step 1108).

As previously mentioned, the present invention applies equally to any type motion sickness beyond seasickness, such as carsickness or airsickness. In one example, a young child is riding in a car while reading a book. As the car turns a corner, the young child may experience a sensory mismatch. The virtual reality system, worn by the young child, detects the acceleration and any yaw, roll or pitch resulting from the car turning a corner, and adjusts the display accordingly. Similarly, a pilot is making a turn with his plane. Instead of displaying on a dial a visual of the airplane's yaw, roll or pitch, the visual reality system acquires information regarding the yaw, roll or pitch, captures data (e.g., what the pilot would normally see in his cockpit), processes said data to account for the yaw, roll or pitch, and displays the processed data for the pilot to see.

Various features, methods, systems, and devices described herein may be combined with features described in U.S. Pat. No. 5,966,680, the entire contents of which are incorporated herein by reference.

It will be apparent to those skilled in the art that such aspects are provided by way of example only. It should be understood that numerous variations, alternatives, changes, and substitutions may be employed by those skilled in the art in practicing the invention.

Accordingly, it will be understood that the invention is not to be limited to the aspects disclosed herein, but is to be understood from the following claims, which are to be interpreted as broadly as allowed under the law.

What is claimed is:

1. A sensory compensation device comprising:
   an orientation and acceleration sensor arranged to generate orientation and acceleration data based on one or more of detected velocity, angular rate, gravity, motion, position, acceleration, and orientation associated with the sensory compensation device;
   wherein the orientation and acceleration data include:
   a differential position between an inertial reference point and a detected orientation and acceleration of the device, and
   at least one of roll, pitch, and yaw data in relation to the inertial reference point;
   an optical sensor arranged to capture real-time images and generate real-time image data of an area adjacent to the sensory compensation device:
   a processor arranged to: i) receive the real-time image data, ii) receive the position and orientation data and iii) generate compensated image data based on the real-time image data and the orientation and acceleration data; and
   a display arranged to display compensated images derived from the compensated image data, wherein a portion of the compensated images includes the captured real-time images with adjusted orientations and accelerations in relation to the captured real-time images, and wherein the portion of compensated images is adjusted proportional to the differential position between the inertial reference point and the detected orientation and acceleration of the device and in a reciprocal direction as the direction of the change in the detected differential position.

2. The sensory compensation device of claim 1, wherein the inertial reference point includes a reference horizon.

3. The sensory compensation device of claim 1, wherein the portion of compensated images is rolled clockwise by one or more degrees proportional to a detected roll of the sensory compensation device by the one or more degrees in a counterclockwise direction.

4. The sensory compensation device of claim 1, wherein the sensory compensation device is one of head-mounted, hand-held, and detachably connectable to an optical system.

5. The sensory compensation device of claim 4, wherein the optical system includes eyeglasses.

6. The sensory compensation device of claim 1, wherein the display includes at least one of LCD, LED, liquid crystal on silicon (LCoS), and OLED elements.

7. The sensory compensation device of claim 1, wherein the area adjacent to the sensory compensation device includes at least one of an area forward, behind, and at a side of the device.

8. The sensory compensation device of claim 1, wherein the optical sensor includes at least one video camera.

9. The sensory compensation device of claim 1, wherein the compensated image data includes data that enables the display of at least one of an overlay, background, and shadow image with respect to the captured real-time images.

10. The sensory compensation device of claim 9, wherein the at least one of the overlay, background, or shadow image includes at least one of a reference horizon and sky.

11. The sensory compensation device of claim 10, wherein the sky is a night sky including one or more stars.

12. The sensory compensation device of claim 1, wherein the compensated images include navigational information.

13. A sensory compensation device comprising:
    an orientation and acceleration sensor arranged to generate orientation and acceleration data based on one or more of detected velocity, angular rate, gravity, motion, position and orientation associated with the sensory compensation device;

wherein the orientation and acceleration data include:

a differential position between an inertial reference point and a detected orientation and acceleration of the device, and at least one of roll, pitch, and yaw data in relation to the inertial reference point:

an optical element through which a user views an area adjacent to the sensory compensation device;

a processor arranged to: i) receive the orientation and acceleration data and ii) generate orientation and acceleration image data; and a display arranged to display orientation and acceleration images derived from the orientation and acceleration image data to the user via the optical element, wherein the orientation and acceleration images include one or more features having adjusted orientations and accelerations in relation to the view of the area adjacent to the sensory compensation device, and wherein the orientation and acceleration images are adjusted proportional to the differential position between the inertial reference point and the detected orientation and acceleration of the device and in a reciprocal direction as the direction of the change in the detected differential position.

14. The sensory compensation device of claim 13, wherein the orientation and acceleration image data includes data that enables the display of at least one of an overlay image on the view of the area adjacent to the device via the optical element.

15. The sensory compensation device of claim 14, wherein the overlay includes at least one of a reference horizon and sky.

16. A computing device comprising:

an orientation and acceleration sensor arranged to generate orientation and acceleration data based on one or more of detected velocity, angular rate, gravity, motion, acceleration and orientation associated with the computing device;

wherein the orientation and acceleration data include:

a differential position between an inertial reference point and a detected orientation and acceleration of the device, and at least one of roll, pitch, and yaw data in relation to the inertial reference point;

a processor arranged to: i) receive the orientation and acceleration data and ii) generate compensated image data based on the orientation and acceleration data; and a display arranged to display compensated images derived from the compensated image data, wherein a portion of the compensated images include one or more features having adjusted orientations and accelerations in relation to a user's view of the area adjacent to the computing device, and wherein the portion of compensated images is adjusted proportional to the differential position between the inertial reference point and the detected orientation and acceleration of the device and in a reciprocal direction as the direction of the change in the detected differential position.

17. The computing device of claim 16, wherein the computing device is one or more of a computer desktop, mobile device, computer where the display is projected via a projector, and portable computer tablet.

18. A hand-held mobile computing device comprising:

an orientation and acceleration sensor arranged to generate orientation and acceleration data based on one or more of detected velocity, angular rate, gravity, motion, position, acceleration, and orientation associated with the hand-held mobile computing device;

wherein the orientation and acceleration data include: a differential position between an inertial reference point and a detected orientation and acceleration of the device, and at least one of roll, pitch, and yaw data in relation to the inertial reference point;

an optical sensor arranged to capture real-time images and generate real-time image data of an area adjacent to the hand-held mobile computing device; a processor arranged to: i) receive the real-time image data, ii) receive the orientation and acceleration data and iii) generate compensated image data based on the real-time image data and the position and orientation data; and a display arranged to display compensated images derived from the compensated image data, wherein a portion of the compensated images includes the captured real-time images with adjusted orientations and accelerations in relation to the captured real-time images, and wherein the portion of compensated images is adjusted proportional to the differential position between the inertial reference point and the detected orientation and acceleration of the device and in a reciprocal direction as the direction of the change in the detected differential position.

* * * * *